United States Patent [19]

Tumer

[11] Patent Number: 5,756,322
[45] Date of Patent: May 26, 1998

[54] POKEWEED ANTIVIRAL PROTEIN MUTANTS

[75] Inventor: Nilgun E. Tumer, Belle Mead, N.J.

[73] Assignee: Rutgers, The State University, Piscataway, N.J.

[21] Appl. No.: 500,611

[22] Filed: Jul. 11, 1995

[51] Int. Cl.$^6$ .......................... A61K 35/78; C07K 14/415
[52] U.S. Cl. ...................... 435/172.1; 530/370; 536/23.6
[58] Field of Search ............................... 435/69.1, 172.1, 435/172.3; 536/23.6; 530/370

[56] References Cited

U.S. PATENT DOCUMENTS 5,304,730  4/1994  Lawson et al. .......................... 800/205

FOREIGN PATENT DOCUMENTS

2699553 A1  6/1994  France .

OTHER PUBLICATIONS

Abel et al., Science 232:738–43 (1986).
Cuozzo et al., Bio/Technology 6:549–57 (1988).
Hemenway et al., EMBO J. 7:1273–80 (1988).
Stark et al., Bio/Technology 7:1257–62 (1989).
Lawson et al., Bio/Technology 8:127–34 (1990).
Kawchuk et al., Mol. Plant–Microbe Interactions 3(5):301–07 (1990).
Lodge et al., Proc. Natl. Acad. Sci. USA 90:7089–93 (1993).
Irvin et al., Pharmac. Ther. 55:279–302 (1992).
Endo et al., Biophys. Res. Comm., 150:1032–36 (1988).
Hartley et al., FEBS Lett. 290:65–68 (1991).
Beachy et al., Ann. Rev. Phytopathol. 28:451–74 (1990).
Golemboski et al., Proc. Natl. Acad. Sci. USA 87:6311–15 (1990).
Hayashi et al., J. Bioenerg. Biomem. 22:451–71 (1990).
Dore et al., Nuc. Acids Res. 21(18):4200–05 (1993).
Monzingo et al., J. Mol. Biol. 233:705–15 (1993).
Chen et al., Plant Pathol. 40:612–20 (1991).

*Primary Examiner*—Elizabeth F. McElwain
*Attorney, Agent, or Firm*—Lerner, David, Littenberg, Krumholz & Mentlik

[57] ABSTRACT

Disclosed are PAP mutants having reduced phytotoxicity compared to wild-type PAP, and which retain wild-type PAP biological activity in plants. One group of PAP mutants is characterized by at least one amino acid substitution in the N-terminus of mature PAP, such as the Glycine 75 residue or the Glutamic acid 97 residue. Another group of preferred PAP mutants is characterized by mutations such as truncations in the C-terminal region of mature PAP. PAP mutants having from at least about 26 to about 76 mature PAP amino acids (not counting the 29-amino acid C-terminal extension of wild-type PAP) exhibit reduced phytotoxicity and retain PAP biological activity in plants. The disclosed PAP mutants may include the 22-amino acid N-terminal signal sequence and/or the C-terminal extension of wild-type PAP.

Also disclosed are DNA molecules encoding the PAP mutants. The DNAs can be operably linked to a promoter functional in given host cells such as plants, and stably transformed into a vector functional in said cells. Procaryotic or eucaryotic hosts, e.g., yeast or plants, stably transformed with a mutant PAP-encoding DNA are further disclosed, as well as protoplasts stably transformed with the DNAs. Transgenic plants and seed containing the DNAs are also provided. The transgenic plants exhibit broad spectrum virus resistance. They include monocots, such as cereal crops, and dicot plants.

Further disclosed is a method for identifying a PAP mutant having reduced phytotoxicity and which retains PAP biological activity. The method involves the steps of providing a eucaryotic cell stably transformed with a mutagenized PAP-encoding DNA molecule, wherein the DNA molecule is operably linked to an inducible promoter functional in eucaryotic cells. The thus-transformed cell is cultured in a suitable medium, and after a predetermined time, an inducer is added to the medium to cause expression of the DNA molecule. A determination is then made as to whether any cultured cells survive the induction of expression of the DNA molecule. The presence of which indicates the presence of a PAP mutant having reduced phytotoxicity so that the biological activity of the PAP mutant encoded by the mutagenized DNA can then be determined. Any PAP mutants which also exhibit broad spectrum virus resistance in an in vivo or in vitro assay would be considered as PAP mutants which retain PAP biological activity in plants. Isolated and purified PAP mutants identified by the aforesaid process are also provided.

17 Claims, No Drawings

5,756,322

1

POKEWEED ANTIVIRAL PROTEIN MUTANTS

GOVERNMENT SUPPORT

The development of this invention was supported in part by National Science Foundation Grant MCB-9419919. Therefore, the Government may have certain rights in the invention.

FIELD OF THE INVENTION

This invention relates generally to agricultural biotechnology, and more specifically to methods and genetic materials for conferring virus resistance to plants.

BACKGROUND OF THE INVENTION

Many commercially valuable agricultural crops are prone to infection by plant viruses. These viruses are capable of inflicting significant damage to a crop in a given season, and thus can drastically reduce its economic value. The reduction in economic value to the farmer in turn results in a higher cost of goods to ultimate purchasers. Several published studies have been directed to the expression of plant virus capsid proteins in a plant in an effort to confer resistance to viruses. See, e.g., Abel et al., Science 232:738–43 (1986); Cuozzo et al., Bio/Technology 6:549–57 (1988); Hemenway et al., EMBO J. 7:1273–80 (1988); Stark et al., Bio/Technology 7:1257–62 (1989); and Lawson et al., Bio/Technology 8:127–34 (1990). However, the transgenic plants exhibited resistance only to the homologous virus and related viruses, but not to unrelated viruses. Kawchuk et al., Mol. Plant-Microbe Interactions 3(5):301–07 (1990), disclose the expression of wild-type potato leafroll virus (PLRV) coat protein gene in potato plants. Even though the infected plants exhibited resistance to PLRV, all of the transgenic plants that were inoculated with PLRV became infected with the virus and thus disadvantageously allowed for the continued transmission of the virus such that high levels of resistance could not be expected. See U.S. Pat. No. 5,304,730.

Lodge et al., Proc. Natl. Acad. Sci. USA 90:7089–93 (1993), report the *Agrobacterium tumefaciens*-mediated transformation of tobacco with a cDNA encoding wild-type pokeweed antiviral protein (PAP) and the resistance of the transgenic tobacco plants to unrelated viruses. PAP, a Type I ribosome-inhibiting protein (RIP) found in the cell walls of *Phytolacca americana* (pokeweed), is a single polypeptide chain that catalytically removes a specific adenine residue from a highly conserved stem-loop structure in the 28S rRNA of eukaryotic ribosomes, interfering with elongation factor-2 binding and blocking cellular protein synthesis. See, e.g., Irvin et al., Pharmac. Ther. 55:279–302 (1992); Endo et al., Biophys. Res. Comm., 150:1032–36 (1988), and Hartley et al., FEBS Lett. 290:65–68 (1991). The observations by Lodge were in sharp contrast to previous studies, supra, which reported that transgenic plants expressing a viral gene were resistant to that virus and closely related viruses only. See also Beachy et al., Ann. Rev. Phytopathol. 28:451–74 (1990); and Golemboski et al., Proc. Natl. Acad. Sci. USA 87:6311–15 (1990). Lodge also reports, however, that the PAP-expressing tobacco plants (i.e., above 10 ng/mg protein) tended to have a stunted, mottled phenotype, and that other transgenic tobacco plants that accumulated the highest levels of PAP were sterile.

Hence, a need remains for a means by which to confer broad spectrum virus resistance to plants which overcomes the problems associated with known methods, and particularly which would require a minimum number of transgenes, the expression of which would not cause plant cell death or sterility.

SUMMARY OF INVENTION

The present invention is directed to PAP mutants having reduced phytotoxicity, and which retain PAP biological activity in plants. One preferred group of PAP mutants is characterized by at least one amino acid substitution in the N-terminus of mature PAP, such as a substitution for the Glycine 75 residue or the Glutamic acid 97 residue. Another preferred group of PAP mutants is characterized by mutations such as truncations in the C-terminal region of mature PAP. More preferred are PAP mutants having from at least about 26 to about 76 mature PAP C-terminal amino acids deleted (not counting the 29-amino acid C-terminal extension of wild-type PAP), and which exhibit reduced phytotoxicity and retain PAP biological activity in plants. The PAP mutants of the present invention may include the 22-amino acid N-terminal signal sequence and/or the C-terminal extension of wild-type PAP.

The present invention also provides DNA molecules encoding the PAP mutants. The DNAs can be operably linked to a promoter functional in procaryotic (e.g., *E. coli*) or eucaryotic cells such as plants, and then stably transformed into a vector functional in said cells. Hosts, e.g., procaryotic or eucaryotic cells (e.g., yeast or plants), stably transformed with a mutant PAP-encoding DNA are also provided, as well as protoplasts stably transformed with the DNAs. Transgenic plants and seed containing the DNAs are also provided. The expression of the DNAs in the transgenic plants confers broad spectrum virus resistance upon the plants without being as phytotoxic to the plant as wild-type PAP. Plants included within the scope of the present invention are monocots, such as cereal crops, and dicot plants.

The present invention further provides a method identifying a PAP mutant having reduced phytotoxicity and which retains PAP biological activity. The method involves the steps of providing a transformed eucaryotic cell such as yeast containing a mutagenized PAP-encoding DNA molecule, wherein the DNA molecule is operably linked to an inducible promoter functional in the eucaryotic cell. The thus-transformed cells are cultured in a suitable medium, and after a predetermined time, an inducer is added to the medium to cause expression of the DNA molecule. A determination is then made as to whether the cultured cells survive the induction of expression of the DNA molecule so that the biological activity of the PAP encoded by the mutagenized DNA can be determined. PAPs which exhibit a substantial lack of toxicity to the host would be considered as PAP mutants which exhibit reduced phytotoxicity. The thus-identified PAP mutants which also exhibit broad spectrum virus resistance as determined by an in vitro or an in vivo assay, would also be considered as PAP mutants which retain PAP biological activity in plants. The present invention further provides isolated and purified PAP mutants identified by the aforesaid process.

DETAILED DESCRIPTION OF THE PREFERRED EMBODIMENTS

Transgenic plants expressing DNAs encoding the PAP mutants of the present invention exhibit reduced phytotoxicity compared to transgenic plants that produce mature, wild-type PAP, ("PAP"), or variant PAP, i.e. PAP-v but also exhibit PAP broad spectrum anti-viral activity. By the term "reduced phytotoxicity," it is meant that the transgenic plant which expresses a mutant PAP-encoding gene exhibits a normal and fertile phenotype and does not exhibit the stunted, mottled phenotype characteristic of transgenic plants that produce mature PAP. See Lodge, supra. By "wild-type PAP," it is meant the PAP amino acid sequence 1-262, the 22-amino acid N-terminal signal peptide ("the N-terminal signal sequence of wild-type PAP"), and the 29 amino acid C-terminal extension (amino acids enumerated 263-291) illustrated in Table 1, below as SEQ. ID No. 2. The corresponding nucleotide sequence is set forth as SEQ. ID No. 1. Thus, by "wild-type, mature PAP," it is meant the PAP amino acid sequence 1-262 shown in Table I.

TABLE I

5'CTATGAAGTCGGGTCAAAGCATATACAGGCTATGCATTGTTAGAAACATTGATGCCT
CTGATCCCGATAAACAATACAAATTAGACAATAAGATGACATACAAGTACCTAAACTG
TGTATGGGGGAGTGAAACCTCAGCTGCTAAAAAAACGTTGTAAGAAAAAAAGAAAGTT
GTGAGTTAACTACAGGGCGAAAGTATTGGAACT

| AGCTAGTAGGAAGGGAAG | | | | ATG Met | AAG Lys | TCG Ser | ATG Met | CTT Leu | GTG Val (67) | GTG Val | ACA Thr | ATA Ile | TCA Ser | ATA Ile |
|---|---|---|---|---|---|---|---|---|---|---|---|---|---|---|
| TGG Trp | CTC Leu | ATT Ile | CTT Leu | GCA Ala | CCA Pro (100) | ACT Thr | TCA Ser | ACT Thr | TGG Trp | GCT Ala | GTG Val (1) | AAT Asn | ACA Thr | ATC Ile | ATC Ile | TAC Tyr |
| AAT Asn | GTT Val | GGA Gly | AGT Ser (10) | ACC Thr | ACC Thr | ATT Ile | AGC Ser | AAA Lys | TAC Tyr | GCC Ala | ACT Thr | TTT Phe | CTG Leu (20) | AAT Asn | GAT Asp | CTT Leu |
| CGT Arg | AAT Asn | GAA Glu | GCG Ala | AAA Lys | GAT Asp | CCA Pro (30) | AGT Ser | TTA Leu | AAA Lys | TGC Cys | TAT Tyr | GGA Gly | ATA Ile | CCA Pro | ATG Met | CTG Leu (40) |
| CCC Pro | AAT Asn | ACA Thr | AAT Asn | ACA Thr | AAT Asn | CCA Pro | AAG Lys | TAC Tyr | GTG Val (50) | TTG Leu | GTT Val | GAG Glu | CTC Leu | CAA Gln | GGT Gly | TCA Ser |
| AAT Asn | AAA Lys | AAA Lys | ACC Thr | ATC Ile | ACA Thr | CTA Leu | ATG Met | CTG Leu | AGA Arg | CGA Arg | AAC Asn | AAT Asn | TTG Leu | TAT Tyr | GTG Val | ATG Met |
| AAT Asn | AAA Lys | AAA Lys (60) | ACC Thr | ATC Ile | ACA Thr | CTA Leu | ATG Met | CTG Leu | AGA Arg | CGA Arg | AAC Asn | AAT Asn (70) | TTG Leu | TAT Tyr | GTG Val | ATG Met |
| GGT Gly | TAT Tyr | TCT Ser | GAT Asp | CCC Pro | TTT Phe (80) | GAA Glu | ACC Thr | AAT Asn | AAA Lys | TGT Cys | CGT Arg | TAC Tyr | CAT His | ATC Ile | TTT Phe (90) | AAT Asn |
| GAT Asp | ATC Ile | TCA Ser | GGT Gly | ACT Thr | GAA Glu | CGC Arg | CAA Gln | GAT Asp (100) | GTA Val | GAG Glu | ACT Thr | ACT Thr | CTT Leu | TGC Cys | CCA Pro | AAT Asn |
| GCC Ala | AAT Asn (110) | TCT Ser | CGT Arg | GTT Val | AGT Ser | AAA Lys | AAC Asn | ATA Ile | AAC Asn | TTT Phe | GAT Asp (120) | AGT Ser | CGA Arg | TAT Tyr | CCA Pro | ACA Thr |
| TTG Leu | GAA Glu | TCA Ser | AAA Lys | GCG Ala (130) | GGA Gly | GTA Val | AAA Lys | TCA Ser | AGA Arg | AGT Ser | CAG Gln | GTC Val | CAA Gln | CTG Leu (140) | GGA Gly | ATT Ile |
| CAA Gln | ATA Ile | CTC Leu | GAC Asp | AGT Ser | AAT Asn | ATT Ile (150) | GGA Gly | AAG Lys | ATT Ile | TCT Ser | GGA Gly | GTG Val | ATG Met | TCA Ser | TTC Phe | ACT Thr |
| GAG Glu | AAA Lys | ACC Thr | GAA Glu | GCC Ala | GAA Glu | TTC Phe | CTA Leu | TTG Leu | GTA Val (170) | GCC Ala | ATA Ile | CAA Gln | ATG Met | GTA Val | TCA Ser | GAG Glu |
| (160) | | | | | | | | | | | | | | | | |
| GCA Ala | GCA Ala | AGA Arg | TTC Phe (180) | AAG Lys | TAC Tyr | ATA Ile | GAG Glu | AAT Asn | CAG Gln | GTG Val | AAA Lys | ACT Thr | AAT Asn | TTT Phe (190) | AAC Asn | AGA Arg |
| GCA Ala | TTC Phe | AAC Asn | CCT Pro | AAT Asn | CCC Pro | AAA Lys (200) | GTA Val | CTT Leu | AAT Asn | TTG Leu | CAA Gln | GAG Glu | ACA Thr | TGG Trp | GGT Gly | AAG Lys (210) |
| ATT Ile | TCA Ser | ACA Thr | GCA Ala | ATT Ile | CAT His | GAT Asp | GCC Ala | AAG Lys | AAT Asn (220) | GGA Gly | GTT Val | TTA Leu | CCC Pro | AAA Lys | CCT Pro | CTC Leu |
| GAG Glu | CTA Leu | GTG Val (230) | GAT Asp | GCC Ala | AGT Ser | GGT Gly | GCC Ala | AAG Lys | TGG Trp | ATA Ile | GTG Val | TTG Leu | AGA Arg (240) | GTG Val | GAT Asp | GAA Glu |
| ATC Ile | AAG Lys | CCT Pro | GAT Asp | GTA Val | GCA Ala (250) | CTC Leu | TTA Leu | AAC Asn | TAC Tyr | GTT Val | GGT Gly | GGG Gly | AGC Ser | TGT Cys | CAG Gln (260) | ACA Thr |
| ACT Thr | TAT Tyr | AAC Asn | CAA Gln | AAT Asn | GCC Ala | ATG Met | TTT Phe | CCT Pro (270) | CAA Gln | CTT Leu | ATA Ile | ATG Met | TCT Ser | ACT Thr | TAT Tyr | TAT Tyr |
| (262) | | | | | | | | | | | | | | | | |
| AAT Asn | TAC Tyr (280) | ATG Met | GTT Val | AAT Asn | CTT Leu | GGT Gly | GAT Asp | CTA Leu | TTT Phe | GAA Glu | GGA Gly (290) | TTC Phe | TGATCATAAACA (SEQIDNO:2) | | | |

TAATAAGGAGTATATATATATTACTCCAACTATATTATAAAGCTTAAATAAGAGGCCGT
GTTAATTAGTACTTGTTGCCTTTTGCTTTATGGTGTTGTTTATTATGCCTTGTATGCTTG
TAATATTATCTAGAGAACAAGATGTACTGTGTAATAGTCTTGTTTGAAATAAAACTTCC
AATTATGATGCAAAAAAAAAAAAAAAAAA3' (SEQIDNO:1)

Table I further shows PAP-v amino acids and corresponding nucleotides in proper alignment with wild-type PAP. Basically, the amino acid sequence of PAP-v differs from that of wild-type PAP in terms of a Leu20Arg (i.e., an arginine residue at position 20 of mature PAP as opposed to a leucine residue) and a Tyr49His substitution. The third change in the PAP-v nucleotide sequence (TCG→TCA codon for the first occurring Ser in the signal sequence) had no effect on the amino acid sequence. Table 1 also shows 5' and 3' non-coding, flanking sequences. Upon expression in eucaryotic cells, the N-terminal 22-amino acid sequence of wild-type PAP is co-translationally cleaved, yielding a polypeptide having a molecular weight of about 32 kD, which is then further processed by the cleavage of the C-terminal 29-amino acids ("the C-terminal extension of wild-type PAP" or "PAP (263–292)"), yielding mature, wild-type PAP (hereinafter "PAP (1-262)") (i.e., that which is isolated from *Phytolacca americana* leaves), having a molecular weight of about 29 kD. See Irvin et al., Pharmac. Ther. 55:279–302 (1992); Dore et al., Nuc. Acids Res. 21(18):4200–05 (1993); Monzingo et al., J. Mol. Biol. 233:705–15 (1993); Turner et al. (in press).

By the phrase "PAP biological activity," it is meant that the expression of a mutant PAP of the present invention in a transgenic plant confers broad spectrum virus resistance, i.e., resistance to or the capability of suppressing infection by a number of unrelated viruses including but not limited to RNA viruses e.g., potexviruses (PVX) (e.g., Hydrangea ringspot virus), potyvirus (PVY), cucumber mosaic virus (CMV), tobacco mosaic viruses (TMV), barley yellow dwarf virus (BYDV), wheat streak mosaic virus, potato leaf roll virus (PLRV), plumpox virus, watermelon mosaic virus, zucchini yellow mosaic virus, papaya ringspot virus, beet western yellow virus, soybean dwarf virus, carrot read leaf virus and DNA plant viruses such as tomato yellow leaf curl virus. See Lodge et al., supra., Tomlinson et al., J. Gen. Virol. 22:225–32 (1974); and Chen et al., Plant Pathol. 40:612–20 (1991). In addition to conferring broad spectrum virus resistance in planta, Applicant believes that the expression of a mutant PAP of the present invention in transgenic plants confers broad spectrum bacterial, fungal and insect resistance to the plants.

The PAP mutants of the present invention can be characterized generally as (1) those which exhibit altered compartmentalization in vivo, and (2) C-terminal mutants including but not limited to deletion or frameshift mutants. The first category of PAP mutants have altered compartmentalization properties in vivo; that is, they are not localized in the same subcellular compartment as wild-type PAP. While not intending to be bound to any particular theory of operation, Applicant believes that these PAP mutants are unable to undergo co-translational processing (to remove the 22 amino acid signal peptide) and/or post-translational processing (to remove the 29-amino acid C-terminal fragment) which results in substantially diminished or negligible phytotoxicity. What is particularly surprising or unexpected about the function of these mutant PAPs in vivo is that the mutations are located within the sequence encoding the mature PAP (1-262), and not within the signal peptide or the 29-amino acid C-terminal extension. In addition, the mutant PAPs are enzymatically active in vitro, indicating that toxicity in vivo is not solely a function of enzymatic activity. Preferred PAP mutants include a conservative point mutation such that wild-type PAP amino acid residue 75 glycine (Gly75) is changed to valine, alanine, isoleucine or leucine, or (2) a conservative or non-conservative point mutation at wild-type PAP amino acid residue 97 Glutamic acid (Glu97).

More preferred PAP mutants are PAP (1-262, Gly75Val) and PAP (1-262, Glu97Lys), the respective DNAs of which can be prepared by changing the wild-type GGT codon for glycine75 to GTT (valine), and the GAA codon for glutamic acid 97 to AAA (lysine). The PAP mutants of the present invention may include the N-terminal 22-amino acid signal peptide of wild-type PAP and/or the 29-amino acid C-terminal extension, both of which are shown in Table I above. What is particularly surprising and unexpected about the function of these N-terminal mutants is that the mutations are not located within the N-terminal signal peptide or the C-terminal extension. Other PAP mutants having altered compartmentalization properties can be identified by the selection method described below. Dore et al., supra, disclose an Arg67Gly PAP mutant (numbered in Dore as Arg 68Gly due to the presence of an N-terminal methionine residue) which is toxic to eucaryotic cells but non-toxic to procaryotic cells such as *E. coli*. Accordingly, this mutant is not included within the scope of the present invention.

The second category of PAP mutants of the present invention have deletions or amino acid substitutions in the C-terminal region of PAP. Applicant has unexpectedly discovered that these mutants are also non-toxic in vivo even though they are enzymatically active in vitro. Preferred mutants have deletions of from about 26 to about 76 amino acids of mature PAP, and more preferred are PAP (1-236)-PAP (1-184), inclusive. Thus, truncations beginning at about amino acid residue 237 of wild-type mature PAP, e.g., PAP (1-236), PAP (1-235), PAP (1-234), PAP (1-233), PAP (1-232), PAP (1-231), PAP (1-230), PAP (1-229), PAP (1-228), PAP (1-227), PAP (1-226), PAP (1-225), PAP (1-224), PAP (1-223), PAP (1-222), PAP (1-221), PAP (1-220), PAP (1-219), PAP (1-218), PAP (1-217), PAP (1-216), PAP (1-215), PAP (1-214), PAP (1-213), PAP (1-212), PAP (1-211), PAP (1-210), PAP (1-209), PAP (1-208), PAP (1-207PAP (1-206), PAP (1-205), PAP (1-204), PAP (1-203), PAP (1-202), PAP (1-201), PAP (1-200), PAP (1-199), PAP (1-198), PAP (1-197), PAP (1-196), PAP (1-195), PAP (1-194), PAP (1-193), PAP (1-192), PAP (1-191), PAP (1-190), PAP (1-189), PAP (1-188), PAP (1-187), PAP (1-186), PAP (1-185), PAP (1-184) are encompassed by the present invention. Deletions shorter than about 26 (i.e., between 1 and 25 amino acids, inclusive) or longer than about 76 mature PAP amino acids are included in the scope of the present invention provided that they are non-toxic to plant cells, which can be determined by the selection method described in detail below, and they confer broad spectrum virus resistance in planta. The latter property can be determined in vitro by inoculating plant parts, e.g. leaves, with the PAP mutant in the presence of virus, or by an in vivo assay wherein a plant transformed with a mutant PAP-encoding DNA is inoculated with virus. Again, while not intending to be bound by any particular theory of operation, Applicant believes that the sequence of PAP amino acids 244Glu-259Cys (shown in Table I), which is homologous to the consensus sequence for the prokaryotic membrane lipoprotein lipid attachment site (Hayashi et al., J. Bioenerg. Biomem. 22:451–71 (1990)), and which is absent from each of the PAP mutants disclosed above, is involved in binding of PAP to phospholipids on endoplasmic reticulum (ER) membranes which facilitates the translocation of PAP into the cytosol of the cell where it inhibits protein synthesis. Disarming this function, e.g., by deletion or by frameshift mutation, will result in a PAP mutant having the instantly disclosed properties.

Dore et al., supra, disclose a Phe195Tyr, Lys211Arg PAP mutant (which numbering is +1 out-of-phase with the numbering used herein due to the N-terminal Met residue required for expression in *E. coli*), which is toxic to eucaryotic cells (such as plants) but non-toxic to procaryotes such as *E. coli*. Accordingly, this PAP mutant disclosed in the Dore publication is not included within the scope of the present invention.

The PAP mutants can be further modified by way of point mutations, additions and deletions provided that the resultant PAP mutant retains reduced phytotoxicity and PAP biological activity as defined herein. For example, the N-terminus may be changed to a methionine residue, either by substitution or addition, to allow for expression of a DNA encoding the mutant PAP in various host cells particularly *E. coli*.

DNAs encoding the mutant PAPs of the present invention can be prepared by mutagenesis of known PAP genes. See Ausubel et al. (eds.), Vol. 1, Chap. 8 in *Current Protocols in Molecular Biology*, Wiley N.Y. (1990). The DNAs may also be prepared via PCR techniques. See *PCR Protocols*, Innis et al. (eds.), Academic Press San Diego, Calif. (1990). The mutant PAP-encoding DNA (e.g., a cDNA) is preferably inserted into a plant transformation vector in the form of an expression cassette containing all of the necessary elements for transformation of plant cells. The expression cassette typically contains, in proper reading frame, a promoter functional in plant cells, a 5' non-translated leader sequence, the mutant PAP DNA, and a 3' non-translated region functional in plants to cause the addition of polyadenylated nucleotides to the 3' end of the RNA sequence. Promoters functional in plant cells may be obtained from a variety of sources such as plants or plant DNA viruses. The selection of a promoter used in expression cassettes will determine the spatial and temporal expression pattern of the construction in the transgenic plant. Selected promoters may have constitutive activity and these include the CaMV 35S promoter, the actin promoter (McElroy et al. Plant Cell 2:163–71 (1990); McElroy et al. Mol. Gen. Genet. 231:150–160 (1991); Chibbar et al. Plant Cell Rep. 12:506–509 (1993), and the ubiquitin promoter (Binet et al. Plant Science 79:87–94 (1991), Christensen et al. Plant Mol. Biol. 12:619–632 (1989); Taylor et al. Plant Cell Rep. 12:491–495 (1993)). Alternatively, they may be wound-induced (Xu et al., Plant Mol. Biol 22:573–588 (1993), Logemann et al. Plant Cell 1:151–158 (1989), Rohrmeier & Lehle, Plant Mol. Bio. 22:783–792 (1993), Firek et al. Plant Mol. Biol. 22:129–142 (1993), Warener et al. Plant J. 2:191–201 (1993)) and thus drive the expression of the mutant PAP gene at the sites of wounding or pathogen infection. Other useful promoters are expressed in specific cell types (such as leaf epidermal cells, meosphyll cells, root cortex cells) or in specific tissues or organs (roots, leaves or flowers, for example). Patent Application WO 93/07278, for example, describes the isolation of the maize trpA gene which is preferentially expressed in pith cells. Hudspeth and Grula, Plant Mol. Biol. 12:579–589 (1989), have described a promoter derived from the maize gene encoding phosphoenolpyruvate carboxylase (PEPC) with directs expression in a leaf-specific manner. Alternatively, the selected promoter may drive expression of the gene under a light-induced or other temporally-regulated promoter. A further alternative is that the selected promoter be chemically regulated.

A variety of transcriptional cleavage and polyadenylation sites are available for use in expression cassettes. These are responsible for correct processing (formation) of the 3' end of mRNAs. Appropriate transcriptional cleavage and polyadenylation sites which are known to function in plants include the CaMV 35S cleavage and polyadenylation sites, the tml cleavage and polyadenylations sites, the nopaline synthase cleavage and polyadenylation sites, the pea rbcS E9 cleavage and polyadenylation sites. These can be used in both monocotyledons and dicotyledons.

Numerous sequences have been found to enhance gene expression from within the transcriptional unit and these sequences can be used in conjunction with the genes of this invention to increase their expression in transgenic plants. Various intron sequences have been shown to enhance expression, particularly in monocotyledonous cells. For example, the introns of the maize Adhl gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop 1:1183–1200 (1987). In the same experimental system, the intron from the maize bronze-l gene had a similar effect in enhancing expression (Callis et al., supra.). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "Ω-sequence"), Maize Chlorotic mottle Virus (MCMV), and Alfalfa Mosaic Virus (AMV) have been shown to be effective in enhancing expression (e.g. Gallie et al. Nucl. Acids Res. 15:8693–8711 (1987); Skuzeski et al. Plant Mol. Biol. 15:65–79 (1990)).

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformations include the nptII gene which confers resistance to kanamycin (Messing and Vierra, Gene 19:259–268 (1982); Bevan et al., Nature 304:184–187 (1983), the bar gene which confers resistance to the herbicide phosphinothricin (White et al., Nucl. Acids Res. 18:1062 (1990), Spencer et al. Theor. Appl. Genet. 79:625–631 (1990), the hph gene which confers resistance to the antibiotic hygromycin (Blochinger & Diggelmann, Mol. Cell Biol. 4:2929–2931), and the dhfr gene, which confers resistance to methotrexate (Fling and Elwell, 1980). Vectors suitable for Agrobacterium transformation typically carry at least one T-DNA border sequence. These include vectors such as pBIN19 (Bevan, Nucl. Acids Res. (1984) and pCIB200 (EP 0 332 104).

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on Agrobacterium include transformation via particle bombardment, protoplast uptake (e.g. PEG and electroporation) and microinjection. The choice of vector depends largely on the preferred selection for the species being transformed. For example, pCIB3064 is a pUC-derived vector suitable for the direct gene transfer technique in combination with selection by the herbicide basta (or phosphinothricin). It is described in WO 93/07278 and Koziel et al. (Biotechnology 11:194–200 (1993)).

An expression cassette containing the mutant PAP gene DNA containing the various elements described above may be inserted into a plant transformation vector by standard recombinant DNA methods. Alternatively, some or all of the elements of the expression cassette may be present in the vector, and any remaining elements may be added to the vector as necessary.

Transformation techniques for dicotyledons are well known in the art and include Agrobacterium-based techniques and techniques which do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described in Paszkowski et al., EMBO J 3:2717–2722 (1984), Potrykis et al., Mol. Gen. Genet. 199:169–177 (1985), Reich et al., Biotechnology 4:1001–1004 (1986), and Klein et al., Nature 327:70–73 (1987). In each case the transformed cells are regenerated to whole plants using standard techniques.

Agrobacterium-mediated transformation is a preferred technique for transformation of dicotyledons because of its high efficiency of transformation and its broad utility with many different species. The many crop species which are routinely transformable by Agrobacterium include tobacco, tomato, sunflower, cotton, oilseed rape, potato, soybean, alfalfa and poplar (EP 0 317 511 (cotton), EP 0 249 432 (tomato), WO 87/07299 (Brassica), U.S. Pat. No. 4,795,855 (popular)). Agrobacterium transformation typically involves the transfer of the binary vector carrying the foreign DNA of interest (e.g. pCIB200 or pCIB2001) to an appropriate Agrobacterium strain which may depend on the complement of vir genes carried by the host Agrobacterium strain either on a co-resident plasmid or chromosomally (e.g. strain CIB542 for pCIB200 (Uknes et al. Plant Cell 5:159–169 (1993)). The transfer of the recombinant binary vector, to Agrobacterium is accomplished by a triparental mating procedure using *E. coli* carrying the recombinant binary vector, a helper *E. coli* strain which carries a plasmid such as pRK2013 which is able to mobilize the recombinant binary vector to the target Agrobacterium strain. Alternatively, the recombinant binary vector can be transferred to Agrobacterium by DNA transformation (Höfgen & Willmitzer, Nucl. Acids Res. 16:9877 (1988)).

Transformation of the target plant species by recombinant Agrobacterium usually involves co-cultivation of the Agrobacterium with explants from the plant and follows protocols known in the art. Transformed tissue is regenerated on selectable medium carrying an antibiotic or herbicide resistance marker present between the binary plasmid T-DNA borders.

Preferred transformation techniques for monocots include direct gene transfer into protoplasts using PEG or electroporation techniques and particle bombardment into callus tissue. Transformation can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4:1093–1096 (1986)).

Patent Applications EP O 292 435, EP O 392 225 and WO 93/07278 describe techniques for the preparation of callus and protoplasts of maize, transformation of protoplasts using PEG or electroporation, and the regeneration of maize plants from transformed protoplasts. Gordeon-Kamm et al., Plant Cell 2:603–618 (1990) and Fromm et al., Biotechnology 11:194–200 (1993), describe techniques for the transformation of elite inbred lines of maize by particle bombardment.

Transformation of rice can also be undertaken by direct gene transfer techniques utilizing protoplasts or particle bombardment. Protoplast-mediated transformation has been described for Japonica-types and Indica-types (Zhange et al., Plant Cell Rep. 7:739–384 (1988); Shimamoto et al. Nature 338:274–277 (1989); Datta et al. Biotechnology 8:736–740 (1990)). Both types are also routinely transformable using particle bombardment (Christou et al. Biotechnology 9:957–962 (1991)).

Patent Application EP 0 332 581 described techniques for the generation, transformation and regeneration of Pooideae protoplasts. Furthermore, wheat transformation has been described by Vasil et al. (Biotechnology 10:667–674 (1992)) using particle bombardment into cells of type C long-term regenerable callus, and also by Vasil et al. (Biotechnology 11: 1553–1558 (1993)) and Weeks et al. (Plant Physiol. 102:1077–1084 (1993)) using particle bombardment of immature embryos and immature embryo-derived callus.

Transformation of monocot cells such as *Zea mays* can be achieved by bringing the monocot cells into contact with a multiplicity of needle-like bodies on which these cells may be impaled, causing a rupture in the cell wall thereby allowing entry of transforming DNA into the cells. See U.S. Pat. No. 5,302,523. Transformation techniques applicable to both monocots and dicots are also disclosed in the following U.S. Pat. Nos.: 5,240,855 (particle gun); 5,204,253 (cold gas shock accelerated microprojectiles); 5,179,022 (biolistic apparatus); 4,743,548 and 5,114,854 (microinjection); 5,149,655, 5,120,657 (accelerated particle mediated transformation); 5,066,587 (gas driven microprojectile accelerator); 5,015,580 (particle-mediated transformation of soy bean plants); 5,013,660 (laser beam-mediated transformation); 4,849,355 and 4,663,292.

The thus-transformed plant cells or plant tissue are then grown into full plants in accordance with standard techniques. Transgenic seed can be obtained from transgenic flowering plants in accordance with standard techniques. Likewise, non-flowering plants such as potato and sugar beets can be propagated by a variety of known procedures. See, e.g., Newell et al. Plant Cell Rep. 10:30–34 (1991) (disclosing potato transformation by stem culture).

The mutant PAP encoding DNAs of the present invention confer broad spectrum virus resistance to any plant capable of expressing the DNAs, including monocots (e.g., cereal crops) and dicots. Specific examples include maize, tomato, turfgrass, asparagus, papaya, sunflower, rye, beans, ginger, lotus, bamboo, potato, rice, peanut, barley, malt, wheat, alfalfa, soybean, oat, eggplant, squash, onion, broccoli, sugarcane, sugar beet, beets, apples, oranges, grapefruit, pear, plum, peach, pineapple, grape, rose, carnation, daisy, tulip, Douglas fir, cedar, white pine, scotch pine, spruce, peas, cotton, flax and coffee.

PAP mutants other than those specifically described above can be identified by a selection system in eucaryotic cells. The method involves providing a eucaryotic cell stably transformed with a mutagenized PAP-encoding DNA molecule, which is operably linked to an inducible promoter functional in the eucaryotic cell. The mutagenesis can be performed in accordance with techniques well known to those skilled in the art, and can be performed prior to or after the transformation. The disadvantage with mutagenizing the DNA after transformation is that the chromosomal DNA of the host could be mutagenized as well. The thus-transformed cell is then cultured in a suitable medium for a predetermined amount of time, e.g., sufficient to cause some growth of the cells, at which time an inducer is added to the medium to cause expression of the mutagenized DNA molecule. If the cultured cell survives the induction of the expression of the mutagenized PAP DNA molecule, which is indicative of the fact that the mutagenesis resulted in the expression of a non-toxic PAP mutant, the PAP mutant can be then assayed in vitro or in vivo to determine whether it retains PAP biological activity, i.e., confers broad spectrum virus resistance in planta. Preferred in vitro assays include eucaryotic translation systems such as reticulocyte lysate systems wherein the extent of the inhibition of protein synthesis in the system caused by the PAP mutant is determined. Preferred host cells are yeast cells such as *Saccharomyces cerevisiae*, as described in greater detail in Example 1, below. This method can also be conducted with a plurality of randomly mutagenized PAP-encoding DNA molecules. The PAP mutants identified as having reduced phytotoxicity and which retain PAP biological activity can then be isolated, purified and sequenced in accordance with standard techniques.

The invention will be further described by reference to the following detailed examples. These examples are provided for purposes of illustration only, and are not intended to be limiting unless otherwise specified.

EXAMPLE 1

A. Construction of yeast expression vectors and analysis of PAP expression in yeast. The full length cDNAs corresponding to PAP and PAP-v disclosed in Lodge et al., and shown in Table 1, were cloned into yeast expression vectors, under the control of the galactose inducible promoter, GAL1. *S. cerevisiae* was chosen as the expression system because yeast has the advantage of supplying eukaryotic cell-specific post-translational modifications. Since yeast ribosomes are sensitive to PAP, a regulated promoter was used to drive the expression of PAP. The cDNAs encoding PAP and PAP-v were cloned into the yeast expression vector pAC55, containing the selectable marker, URA3, as BglII/SmaI fragments under the control of the galactose inducible promoter pGall. The vectors containing PAP (NT123) and PAP-v (NT124) were transformed into the yeast strain W303 (Mat a, ade2-1 trp1-1 ura3-1 leu2-3,112 his3-11, 15can1-100 )(Bossie et al., Mol. Biol. Cell, 3:875–893 (1992)), according to the procedure described in Ito et al., J. Bacteriol. 153:163–168 (1983), and transformants were selected on uracil minus medium with glucose at 30° C.

Yeast cells containing either NT123 (wild-type PAP) or NT124 (PAP-v) were grown in uracil minus medium with 2% raffinose at 30° C. for 48 h to a density of $5\times10^7$ cells/ml. PAP protein expression was induced by the addition of 2% galactose to half of the culture, while the other half of the culture was used as an uninduced control. The cells were allowed to grow for an additional 4 h and then collected by centrifugation at 10,000 g for 5 min. The cells were resuspended in RIPA buffer 9150 mM NaCl, 1% NP-40, 0.5% sodium deoxycholate, 0.1% SDS, 50 mM Tris-HCl, pH8) with protease inhibitors (0.1 μg/ml each of antipain, aprotinin, chymostatin, leupeptin, pepstatin) and lysed using glass beads (0.5 mm). Extracts were loaded on a 10% SDS-PAGE gel in accordance with the procedures described in Tomlinson, supra. Immunoblot analysis was performed by the enhanced chemiluminescence (ECL) method (Amersham), using antibodies against purified PAP.

Both PAP and PAP-v were expressed in yeast after galactose induction. Based on comparison with PAP protein standards, yeast cells containing the PAP plasmid (NT123) expressed both the mature form of PAP and a larger form, while cells containing the PAP-v (NT124) expressed predominantly the larger form and very low levels of the mature form. PAP was not detected in the culture medium. These results suggest that: (1) PAP is expressed as a precursor and processed to the mature form in yeast; and (2) PAP undergoes further processing in addition to the co-translational cleavage of the amino acid N-terminal signal peptide (Lodge et al., supra.) because the size of the mature PAP and the PAP expressed in yeast was found to be smaller than the expected size after the removal of the signal sequence.

B. In vitro translation and processing of PAP and PAP-v. To examine the processing of PAP in vitro, both constructs described in Example 1A were transcribed and translated in vitro using the T7 coupled reticulocyte lysate translation system in the presence of 35S-methionine with or without canine microsomal membranes (Promega). PAP and PAP-v cDNAs were cloned into the pGem 3Z vector (Promega) downstream of the T7 promoter. An equal amount of DNA (1 μg) from each construct was transcribed and translated in vitro in the presence $^{35}$S-methionine, using the T7 coupled reticulocyte lysate translation system (Promega) with or without canine pancreatic microsomal membranes (Promega). Translation products were incubated with 0.2 mg/ml proteinase K in the presence of 5 mM EDTA and 125 mM sucrose for 90 min. Proteinase K was inactivated by addition of 4mM PMSF and incubation at room temperature for 2 hours. Translation products were then treated with Endo-H (endo-N-acetylglucosaminidase) (1 mU/10 μl) in the presence of 0.1% SDS and 0.1M sodium citrate pH 5.5, at 37° C. for 12 hours. Equal amounts of protein (3.5 μl) were analyzed on 10% SDS-PAGE in accordance with the procedure described in Laemmli et al., Nature (London) 227:680–685 (1970).

PAP and PAP-v encode precursor proteins of 33 and 34 kD, respectively, and both precursors are processed to a 32 kD form after incubation with membranes. The processed proteins are still larger than the mature form (29 kD), indicating that the PAP precursor undergoes further post-translational processing. PAP does not contain any N-linked glycosylation sites and the size of the in vitro translated proteins did not change after treatment with Endo H which removes carbohydrate. These results indicated that the PAP precursors contain an N-terminal signal sequence which is co-translationally processed, and another sequence, which is post-translationally removed. Further evidence for C-terminal processing was obtained from X-ray structure analysis, which showed that mature PAP is 29 amino acids shorter at its C-terminus than the sequence predicted from the cDNA. See Monzingo et al., J. Mol. Biol. 2:705–715 (1993).

C. Growth of transformed yeast: In the presence of 2% raffinose, a non-repressing, non-inducing carbon source relative to GAL gene expression, the growth of yeast transformants containing NT 123 or NT124 was indistinguishable from the transformants containing the vector alone. Growth of transformed yeast containing NT123 was arrested upon addition of the inducer, galactose, to the medium. Cells containing NT123 or NT124 did not grow on plates containing galactose. In the liquid medium, however, the extent of inhibition was greater with NT123 than NT124, possibly due to lower levels of mature PAP produced in yeast containing NT124. PAP expression was detected within 2 h of galactose addition to the medium. Maximal levels were reached in 6 to 8 h. Immunoblot analysis using antibodies against PAP, detected a maximal PAP level of 1 μg/mg yeast protein in NT123 transformants and 250 ng/mg yeast protein in NT124 transformants. These results were consistent with production of active PAP in yeast.

D. Mutagenesis of PAP plasmids. To isolate PAP mutants nontoxic to yeast, the expression plasmids containing PAP (NT123) or PAP-v (NT124) were mutagenized using hydroxylamine, transformed into yeast and cells were plated on medium containing glucose and replica plated to galactose containing plates. About 10 μg of the purified plasmid DNA were added to 500 μl of freshly prepared hydroxylamine solution (0.35 g hydroxylamine-HCl and 0.09 g NaOH in 5 ml of water) and incubated at 37° C. for 20 h. To stop the mutagenesis, 10 μl of 5M NaCl, 50 μl of 1 mg/ml BSA and 1 ml of 100% ethanol were added and the mutagenized DNA was precipitated by incubation at −70° C. for 10 minutes. The DNA was resuspended in TE and precipitated again. The DNA was then transformed into yeast and plated on uracil minus medium containing 2% glucose and replica plated on medium containing 2% galactose. The colonies that grew on galactose were analyzed for PAP expression by ELISA described in Lodge et al., supra., and by immunoblot analysis to identify the mutants which expressed hydroxylamine generated mutant PAP.

E. Growth of mutant yeast: Growth of mutants derived from NT123 on galactose containing medium was indistinguishable from growth on raffinose containing medium. Similar results were obtained with mutants derived from NT124. Analysis of protein accumulation in yeast indicated that the expression of wild type PAP, but not the hydroxylamine generated mutant PAP, resulted in decreased protein accumulation in yeast (data not shown).

After mutagenesis, the colonies growing on uracil deficient galactose plates were analyzed for PAP expression by ELISA using PAP antibodies and the positives were further analyzed by imunoblot analysis. Of a total of 28 mutants from NT123 mutagenesis, six different isolates expressed proteins which cross-reacted with PAP antibodies. Out of 44 mutants isolated from NT124 mutagenesis, 24 different isolates produced proteins which cross-reacted with PAP antibodies. Four mutants (HMNT123-1, 124-6, 124-7, and 124-1) produced proteins which were larger than the mature form of PAP (29 kD), suggesting that the processing of PAP to the mature form is blocked in these mutants. Two mutants (HMNT123-2 and 123-3) produced proteins that co-migrated with the mature form of PAP, while several others (HMNT123-4, 123-5, 123-6, 124-2 and 124-3), produced smaller proteins. The protein expression levels in the mutants ranged from 0.005 to 0.08% of total soluble protein.

F. Nucleotide sequence analysis of PAP mutants: The positions of the amino acid alterations in the PAP mutants were identified by sequence analysis of the plasmids rescued from yeast. Plasmids were isolated from the mutants, transformed into *E. coli* according to the procedure set forth in Rose et al., supra., and sequenced using the Sequenase 2.0 DNA sequencing kit (USB). See Robzyk et al., Nucl. Acids Res. 20, 3790 (1992). Sequence analysis of HMNT123-2 revealed that it contains a single point mutation, changing the glutamic acid at position 176 to valine(E176V) at the putative active site (Table II). Hmnt123-2 produced a protein of the same size as the wild type PAP. Glutamic acid at position 176 (E176) is highly conserved among all RIPs sequenced to date and it is proposed to be at the active site cleft of PAP. See Stevens et al., Experientia 37:257–259 (1981). HMNT123-6, HMNT124-2 and HMNT124-3 all had a point mutation near the C-terminus which introduced a stop codon instead of a tryptophan at position 237 (W237) (Table II). As a result of this mutation, 26 amino acids were deleted from the C-terminus of the mutant PAP, and a truncated protein was produced. HMNT123-5 contained a frameshift mutation, which deleted two nucleotides (GA) at about the codon for Glu184 (GAG), whereby the reading frame was altered and the Asn190 codon became TAA, because the reading frame shifted to the −1 position, resulting in expression of a truncated protein, i.e., PAP (1-184, SGEN). A point mutation in HMNT124-1 changed the glutamic acid at position 97 to lysine (E97K) (Table I). HMNT123-1 also contained a single point mutation, at position 75, changing glycine to valine (G75V). Both of these mutants expressed a larger protein than purified mature PAP, suggesting that processing of PAP is inhibited in these mutants.

To confirm that the observed mutant phenotypes were due to the mutations identified in the PAP sequence, and not due to a chromosomal mutation, each mutant PAP plasmid was isolated and retransformed into the host strain, W303, and URA+ transformants were selected. These transformants grew at wild type rates on galactose containing medium, indicating that the ability of the transformants to survive induction of PAP expression is plasmid-linked.

TABLE II

| Mutations which abolish the toxicity of PAP to eucaryotic cells | |
|---|---|
| HMNT123-1 | Gly-75 (GGT) → Val (GTT) |
| HMNT123-2 | Glu-176 (GAG) → Val (GTG) |
| HMNT123-4 | Trp-208 (TGG) → Stop (TAG) |
| HMNT123-5 | Glu-184 (GAG) → Glu (GAA) |
| HMNT123-6 | Trp-237 (TGG) →> Stop (TAG) |
| HMNT124-1 | Glu-97 (GAA) → Lys (AAA) |
| HMNT124-2 | Trp-237 (TGG) → Stop (TAG) |
| HMNT124-3 | Trp-237 (TGG) → Stop (TAG) |
| HMNT124-13 | Leu-202 (CTT) → Phe (TTr) |

G. Enzymatic activity of PAP mutants: An in vitro translation assay was used to compare the enzymatic activity of PAP mutants. Brome mosaic virus (BMV) RNA was translated in the rabbit reticulocyte lysate system (Promega) in the presence of extracts from yeast containing different amounts of PAP, as described in Lodge et al., supra. PAP levels in yeast were quantitated by ELISA (Lodge et al., supra.). The inhibition curves were linear in the range of 0.1 to 1 ng PAP/ml. Table III shows the results of the protein synthesis inhibition assay carried out in the presence of 0.2 ng/ml PAP from yeast. The amount of total protein and PAP were adjusted to 87 ng/ml and 0.2 ng/ml, respectively in each extract by adding either wild type yeast extract or RIPA buffer. In previous experiments, when in vitro translation was performed in the presence of 0.2 ng/ml BSA, no inhibition of translation was observed. When 0.2 ng/ml protein from nontransformed yeast (WT) were added, a slight inhibition of translation was observed. Translation was inhibited in the presence of 0.2 ng/ml of: (1) purified PAP added to wild type yeast extract (WT+PAP); (2) protein extracts from yeast containing NT123 or NT124; and (3) protein extracts from yeast containing the hydoxylamine generated mutants HMNT123-3, HMNT124-1, HMNT124-3 and HMNT124-13. In contrast, protein extracted from HMNT123-2 did not inhibit protein synthesis in the reticulocyte lysate system. Similar results were obtained when in vitro translation experiments were performed using 0.1 ng/ml PAP.

15

TABLE III

Inhibition of protein synthesis by PAP mutants

| Protein added to translation medium (protein incorporated) | Protein synthesis (cpm) |
|---|---|
| No RNA | 2,246 +/− 204 |
| BSA | 244,956 |
| WT | 176,723 ± 713 |
| PAP + WT | 146,660 ± 2474 |
| NT123 | 110,007 ± 445 |
| HMNT123-2 | 213,952 ± 767 |
| HMNT123-3 | 134,202 ± 5522 |
| HMNT124 | 84,959 ± 661 |
| HMNT124-1 | 119,529 ± 2094 |
| HMNT124-3 | 132,955 ± 3739 |
| HMNT124-13 | 145,899 ± 4457 |

EXAMPLE 2

Expression of PAP mutants in transgenic tobacco

Mutant PAPs were engineered for constitutive expression in plants to determine if they would be non-toxic to plants, and if they could retain PAP antiviral properties.

In order to insert the PAP genes into the plant expression vectors, the plasmid DNA encoding the mutant PAPs was isolated from yeast, transformed into *E. coli* as described in the Example 1. The plasmid DNA encoding the mutant PAPs was isolated from *E. coli* digested with HindIII, the HindIII site was filled in with klenow DNA polymerase and the plasmid was digested with SacI to isolate the 772 bp SacI/HindIII fragment encoding the mutant PAP. The SacI/HindIII fragments encoding the mutant PAPs were cloned into pMON8443 (Lodge et al., Proc. Natl. Acad. Sci. USA 90:7089–7093 (1993)) after digestion with SacI and SmaI to remove the wild type PAP cDNA inserts. The SacI/HindIII fragment from HMNT123-2 was cloned into SacI/SmaI digested pMON8443 to generate NT144 and the SacI/HindIII fragment from HMNT124-3 was cloned into SacI/SmaI digested pMON8443 to generate NT145. NT146 and NT147 were generated by replacing the 772 bp SacI/HindIII fragment of the wild type PAP cDNA insert in pMON 8443 with the 772 bp SacI/HindIII fragment of HMNT123-2 and HMNT124-3, respectively.

Plasmids NT144, NT145, NT146 and NT147 were mobilized into the ABI strain of *Agrobacterium tumefaciens* for transformation into tobacco and potato (Lodge et al., 1993). For transformation of *N. tabacum*, young leaves from one month old tobacco plants were covered with water for 20–30 min. The water was drained off and the leaves were covered with 10% chlorox and 0.04% Tween 20 for 15 minutes and then rinsed three times with water. Leaf disks were cut with an autoclaved single hole punch and placed upside down on MS104 medium (4.4 g/l MS salts, 30 g/l sucrose, B5 vitamins, 0.1 mg/l NAA and 1.0 mb/l BA) for 1 day for preculture. The precultured disks were placed in a 50 ml tube and inoculated with an overnight culture of Agrobacterium that was diluted 1:5. The tube was inverted several times. The disks were then taken out and blotted on sterile filter paper and placed upside down on MS104 feeder plates with a filter disk to co-culture for 2 days. Leaf disks were then transferred to MS104 media with selection (100 μg/ml kanamycin and 300 μg/ml cefataxime) and placed in an incubator. Calli and shoots appeared in about three weeks. Shoots were transferred to plantcons with MSO media (4.4 g/l MS salts, 30 g/l surose and B5 vitamins) with selection. Roots formed in two weeks, rooted shoots were then transferred to soil and kept in a high humidity environment. The regenerated plants were then screened by ELISA for the presence of neomycin phosphotransferase (NPTII) to identify the expressors.

Transformation frequencies of *N. tabacum* cv Samsun typically range between 10 to 12% (number of transgenic plants obtained per leaf disk). As previously reported the transformation frequency of *N. tabacum* was significantly reduced when vectors containing the wild type PAP (pMON8443) or the variant PAP (pMON8442) were used in transformation (Lodge et al., 1993). In contrast, as shown below in Table IV, no decrease in transformation frequency was observed when vectors containing the nontoxic mutant PAPs were used in the transformation.

TABLE IV

| Plasmid | Frequency of transformation |
|---|---|
| NT144 | 13% |
| NT145 | 11% |
| NT147 | 12% |

As previously reported, the transgenic plants expressing wild type PAP or the variant PAP showed growth reduction, chlorosis and mottling on their leaves (Lodge et al., 1993). In contrast, the transgenic plants expressing the mutant PAPs were phenotypically normal. They grew at the same rate as the wild type plants and showed no chlorosis or mottling on their leaves, indicating that the expression of the mutant PAPs is not toxic to transgenic plants. The mutant PAPs were also expressed in *E. coli* and their expression did not affect the growth rate of *E. coli* cells, indicating that they are not toxic to *E. coli*.

EXAMPLE 3

Antiviral activity of mutant PAP expressed in transgenic tobacco

Transgenic tobacco (*N. tabacum* cv Samsun) plants were assayed by ELISA (Lodge et al., 1993) to determine the level of expression of the mutant PAPs. In Table V, the level of expression of the mutant PAP is compared with the level of expression of the variant PAP (pMON8442) (Lodge et al., 1993) expressed in transgenic plants.

TABLE V

Level of PAP expression in transgenic tobacco

| Plant number | Level of expression |
|---|---|
| NT144-12 | 1.5 μg/mg |
| NT144-13 | 0.9 μg/mg |
| NT145-13 | 4.4 ng/mg |
| pMON8442(26139-11) | 9.6 ng/mg |

As shown in Table V, the transgenic plant containing the C-terminal deletion mutant (NT145-13) expressed similar levels of mutant PAP as the plant expressing the PAP variant (pMON8442) (Lodge et al., 1993). In contrast, transgenic plants containing the active site mutant (NT144) expressed significantly higher levels of the mutant PAP.

To test if the PAP mutants (the NT144 and NT145 constructs) had antiviral activity in vitro, wild type tobacco plants were inoculated with potato virus X (PVX) in the presence of protein extracts from plants expressing the mutant PAP, the PAP-v (pMON8442) and nontransformed (wild type) tobacco. PAP levels in the transgenic plants were quantitated by ELISA. The level of PAP expression in line 145-13 was 4.4 ng/mg and the level of PAP expression in line 144-12 was 1.5 µg/mg. Plants were inoculated with extracts from transgenic plants containing 5 ng PAP per leaf and 1.1 mg total protein. Protein extract was prepared from nontransformed tobacco leaves (WT). Fifty µl of 1 µg/ml PVX was inoculated onto tobacco leaves in the presence of different amounts of total protein from nontransformed tobacco, ranging from 6.7 µg to 1.1 mg. Twenty tobacco plants were inoculated with 50 µl of 1 µg/ml PVX in the presence of 6.7 µg—1.1 mg of total protein from nontransformed plants. As shown in Table VI, all WT plants became infected with PVX and showed local lesions, systemic symptoms and virus accumulation in the leaves above the inoculated leaves (systemic leaves). These results demonstrate that protein extracts from nontransformed tobacco plants do not have any effect on PVX infection. When protein extract from nontransformed tobacco plants was used in the presence of 5 and 10 ng purified PAP (WT+PAP), lower numbers of PVX lesions were observed on inoculated leaves, indicating that tobacco plants were protected from PVX infection in the presence of purified PAP. However, although fewer lesions were obtained on the inoculated leaves of these plants, they showed systemic symptoms and similar levels of PVX antigen as the plants inoculated with PVX in the presence of extracts from nontransformed tobacco plants (WT).

When PVX was inoculated in the presence of 5 ng protein from the transgenic plant (26139) expressing the variant PAP pMON8442, significantly lower numbers of lesions were observed on the inoculated leaves and these plants escaped systemic infection. Similarly, when PVX was inoculated in the presence of 5 ng protein from transgenic plant (145-13) expressing the C-terminal deletion mutant, significantly fewer lesions were obtained. These plants did not show systemic symptoms and the PVX antigen levels were significantly reduced on the inoculated leaves. In contrast, when PVX was inoculated in the presence of 5 to 100 ng protein from transgenic plant expressing the active site mutant (144-12), the numbers of lesions observed on the inoculated leaves was similar to the numbers of lesions observed on plants inoculated in the presence of protein from nontransformed tobacco plants (WT). Systemic symptoms were observed on these plants and PVX antigen levels in the systemic leaves were comparable to the antigen levels in plants inoculated with PVX in the presence of extracts from nontransformed tobacco plants. These results demonstrate that the C-terminal deletion mutant which is enzymatically active in vitro retains its antiviral activity in vitro. In contrast, the active site mutant which is enzymatically inactive in vitro, does not retain its antiviral activity in vitro, suggesting that the enzymatic activity of PAP is critical for antiviral activity in vitro.

Table VI: Effects of PAP mutants on PVX infection of tobacco leaves. Twenty plants for wild-type(wt), ten plants for wt+PAP and five plants for each transgenic protein extract were used. Two leaves from each plant were inoculated with 50 µl of PVX (1 µg/ml) in the presence of different amount of PAP or PAP mutants.

| Plant Extract[a] level (ng/mg)[c] | PAP ng/(leaf) | mean no. of lesions[b] | PVX antigen |
|---|---|---|---|
| WT[d] | 0 | 66.6 ± 10.1 | 4.4 ± 1.4 |
| WT + PAP[e] | 5 | 9.0 ± 2.0 | 3.1 ± 1.9 |
| . | 10 | 1.5 ± 2.0 | 2.8 ± 2.6 |

-continued

| Plant Extract[a] level (ng/mg)[c] | PAP ng/(leaf) | mean no. of lesions[b] | PVX antigen |
|---|---|---|---|
| 26139 | 5 | 1.8 ± 2.9 | NA |
| 145–13 | 5 | 12.5 ± 7.4 | 0.2 ± 0.3 |
| 144–12 | 5 | 57.8 ± 7.4 | 3.2 ± 2.5 |
|  | 10 | 56.1 ± 4.9 | 2.5 ± 1.4 |
|  | 20 | 55.5 ± 13.8 | 4.3 ± 1.4 |
|  | 50 | 53.3 ± 14.9 | 2.8 ± 0.3 |
|  | 100 | 68.0 ± 11.7 | 3.0 ± 0.9 |

[a]Plant extract was prepared from either non-transformed or transformed tobacco leaves with plant expression vector (pMON8442, NT145, and NT144).
[b]The number of lesions were counted at 9 days post-inoculation.
[c]Three leaf discs in a tube were taken from 1st, 2nd and 3rd systemic leaves at 12 days post inoculation and then homogenized in ELISA buffer. The average levels of PVX antigen were quantified by ELISA. The amount of total proteins in each extract were quantified by BCA reagent (Pierce).
[d]Protein extract was made from non-transformed tobacco leaves.
[e]PAP (Calbiochem) was added to a protein extract from non-transformed tobacco leaves.

EXAMPLE 4

Expression of PAP mutants in transgenic potato

Potato stems are cut into 3 mm pieces and placed in sterile water. Agrobacterium containing T144, Nt145, NT146 and NT147 was grown overnight. Cells were spun down and resuspended in 10 ml of water. Agrobacterium was diluted again 1:10 in water. Water was removed from potato stem explants and the diluted Agrobacterium was added. The stem explants were incubated with Agrobacterium for 15 min. The bacteria were removed and the explants were placed on 1/10 MSO plates that had been covered with sterile Whatman #1 filters. MSO contains 4.4 g MS salts, 30 g sucrose and 1 ml B5 vitamin (500X) in a 1 liter volume, pH 5.7. After a two day co-culture period in the dark, the explants were placed on PC media, containing MSO plus 0.5 mg/l zeatin riboside (ZR).5 mg/l $AgNO_3$ and 0.1 mg/l NAA (naphthaleneacetic acid) 100 mg kanamycin and 300 mg cefataxime per liter, for four weeks. After 4 weeks, the explants were placed on PS media which contains MSO plus 5 mg/l ZR, 0.3 mg/l giberellic acid, 100 mg kanamycin and 300 mg cefataxime per liter. Shoots began to appear in four to eight weeks. Shoots were then removed and placed in plantcons containing PM media (4.4 g MS salts, 30 g sucrose, 0.17 g $NaH_2PO_4H_2O$, 1 ml thiamine HC1 and 0.1 g inositol in a 1 liter volume, pH 6.0 and 0.2% Gelrite agar). Plants were then placed in soil, hardened off and analyzed by NPTII ELISA to identify the transgenic plants. Transgenic potato plants were then analyzed by ELISA for PAP expression. Transgenic potato plants expressing NT144, NT145 and NT 146 were identified by ELISA. The transformation frequencies were not affected when constructs containing mutant PAPs were used and the transgenic plants expressing mutant PAPs were phenotypically normal, indicating that the expression of the mutant PAPs is not toxic to potato.

EXAMPLE 5

Expression of PAP mutants in Transgenic Turfgrass

Mutant PAPs were engineered for constitutive expression in monocots. Creeping bentgrass (*Agrostis palustris,* Huds.), which is a turfgrass used in golf courses, fairways, tees and lawns, was used as the monocot species for transformation. In order to construct an expression vector for monocots, NT168 was created by cloning the promoter and the first intron of the maize ubiquitin gene (Toki et al., Plant Physiol.

100:1503–1507 (1992)) into pMON969. pMON969 was digested with HindIII and BglII to remove the CaMV 35S promoter region. The plasmid pAHC20, containing the ubiquitin promoter and the first intron (Toke et al., 1992) was digested with HindIII and BamHI to isolate the 2016 bp HindIII/BamHI fragment which was ligated to HindIII/BglII fragment of pMON969 to generate NT168. The cDNA fragments encoding the mutant PAPs were isolated by digesting NT144 and NT145 with BglII and BamHI and cloned into the BamHI site of NT168. The monocot expression vectors containing the mutant PAP cDNAs were then used in transformation along with pSLJ2011, which contains the selectable marker, the bar gene (Hartmann et al., Biotechnology 12:919–923 (1994). Turfgrass transformation was carried out using two different methods, biolistic transformation using the particle gun and by protoplast transformation as described below.

Embryogenic callus cultures were initiated from surface sterilized seeds of 7 creeping bentgrass cultivars: 'Cobra', 'Emerald', 'PennLinks', 'Providence', 'Putter', 'Southshore', and 'SR1020' and used in biolistic transformation, as described in Hartmann et al. Callus initiation media were MS basal medium and MS vitamins, supplemented with 100 mg $L^{-1}$ myo-inositol, 3% sucrose, and either 150 mg $l^{-1}$ asparagine and 2 mg $L^{-1}$ 2,4-D for MSA2D, or 500 mg $L^{-1}$ casein hydrolysate, 6.6 mg $L^{-1}$ dicamba, and 0.5 mg $L^{-1}$ 6-BA for MMS. Media were solidified with 0.2% Phytagel® (Sigma). After 4 to 6 weeks in the dark at 25° C., embryogenic callus lines were selected and transferred to fresh medium. Suspensions were established from embryogenic callus cultures by adding 1 to 2 g callus to 250 ml flasks with 50 ml liquid media, incubate in the dark at 25° C. with shaking at 120 rpm and subcultured twice a week.

Plates were prepared for particle bombardment by placing 1 ml of suspension cells on 5.5 cm filter disks in plates containing MSA2D media with the addition of 0.4M mannitol. Plates were prepared 20 h prior to bombardment and kept in the dark. Gold particles were prepared by heating at 95° C. in 100% ethanol for 30 min, centrifuged briefly and resuspended in fresh ethanol. The particles were sonicated for 10–30 min in a water bath, washed 3 times in sterile, distilled water, and resuspended in water. DNA samples consisting of 50 µl (5 mg) gold suspensions, 10 µg target DNA, 50 µl 2.5M $CaCl_2$, and 20 µl 0.1M spermidine, were vortexed, centrifuged, and resuspended in ethanol. The ethanol wash was repeated for a total of 3 times. The final pellet was resuspended in 30 µl ethanol, and 5 µl of DNA solution were used per shot. Bombardment was carried out using the Bio-Rad PDS-1000, He Biolistic Delivery System at 1100 psi. Calli from the bombardment experiments were plated out on MSA2D medium containing 2 or 4 mg/l of bialaphos for selection 3–4 days after bombardment and continued for 8 weeks without transfer. After 8 wks on plate selection, calli were transferred to MS media without hormones for regeneration. Regenerates appeared within 2–8 weeks. Shoots were transferred to Plantcons® containing MS medium and roots appeared within 2–4 weeks.

For protoplast transformation, protoplast isolation was performed four days after subculture. Cells were incubated with filter-sterilized enzyme solution containing 1% (w/v) Cellulase Onozuka RA (Yakult Pharmaceutical Co. LTD), 0.1% Pectolyase Y-23 (Seishin Pharmaceutical Co. LTD), and 0.1% MES (2-[N-morpholino]ethane-sulfonic acid) (Sigma) in culture media (MSA2D or MMS with 5% mannitol) for 4 hours at 28° C. with shaking at 50 rpm. About 1 g fresh weight of suspension cultures was treated with 10 ml of enzyme solution. Protoplasts were filtered through Miracloth and washed twice with culture medium containing 5% mannitol. Mannitol was used as an osmotic stabilizing agent. Protoplasts were cultured using a feeder layer system (Rhodes et al., 1988). The washed, filtered protoplasts were pipetted onto a black nitrocellulose membrane (Lee et al., 1989) placed over a feeder layer of suspension cells which had been spread on 5% mannitol culture medium. One week later, the membranes with protoplasts were transferred to a fresh feeder layer on 3% mannitol culture plates. Protoplasts were removed from the feeder layer 2 weeks after isolation. Plating efficiency was determined by dividing the number of visible colonies 3 weeks after isolation by the total number of protoplasts plated. Plants were regenerated by placing protoplast derived calli on MS medium without hormone or with 1 mg $L^{-1}$ 6-BA orkinetin. After 4 to 5 weeks shoots were transferred to Plantcon® with MS medium containing no hormone for rooting. Protoplasts were transformed using either PEG following the protocol of Negrutiu et al., (1987), or electroporation at 170 volts $cm^{-1}$ using a Gene-Pulster (Bio-Rad). In PEG experiments, freshly isolated protoplasts were resuspended at a density of $1 \times 10^7$ protoplasts per ml in 5% mannitol containing 15 mM $MgCl_2$ and 0.1% MES. Approximately 0.3 ml protoplasts were incubated with 20 to 40 µg plasmid DNA and 13% PEG for 10 to 15 min., diluted stepwise and resuspended in culture medium with 5% mannitol (pH 5.8) after centrifugation. In electroporation experiments, protoplasts were resuspended at a density of $5 \times 10^6$ protoplasts per ml in cold filter sterilized electroporation buffer containing 5.2 g $L^{-1}$ KCl, 0.835 g $L^{-1}$ $CaCl_2$, 0.976 g $L^{-1}$ MES and 5% mannitol at pH 5.8. About 0.8 ml protoplasts were mixed with 20 µg DNA by inversion, electroporated at 170 volts $cm^{-1}$ and placed on ice for 15 min., then diluted to a total of 3 ml with culture medium containing 5% mannitol. Selection with 4 mg $L^{-1}$ of bialaphos was initiated 16 days after protoplast isolation and transformation. Resistant colonies were selected on MS medium without hormone, with 6-BA or kinetin as described above. Shoots were transferred to Plantcons® for rooting. A commercial formulation of bialaphos under the trade name Herbiace® (Meiji Seika Kaishya, LTD.) was used in greenhouse herbicide tests. Herbicide rates for Herbiace® were established using control plants, and were based on the commercial rate of 0.75 lb AI/acre (1× the field rate). The herbicide was applied to all the tillers above ground with an artist's paint brush at the rate of 120 ml per flat. Dimension of the flat is 0.1431 $m^2$ and it holds 96 or 24 plants.

Copending patent applications entitled "BIOTHERAPEUTIC AGENTS COMPRISING RECOMBINANT PAP AND PAP MUTANTS" to Fatih Uckun and Nilgun Tumer, U.S. patent application Ser. No. 08/501,253, and "DNAs ENCODING POKEWEED ANTIVIRAL PROTEIN MUTANTS" to Nilgun Tumer, U.S. patent application Ser. No. 08/500,694, filed of even date herewith, are herein incorporated by reference in their entireties.

All publications and patent applications mentioned in this specification are indicative of the level of skill of those skilled in the art to which this invention pertains. All these publications and patent applications are herein incorporated by reference to the same extent as if each individual publication or patent application was specifically and individually indicated to be incorporated by reference.

Various modifications of the invention described herein will become apparent to those skilled in the art. Such modifications are intended to fall within the scope of the appending claims.

I claim:

1. A PAP mutant having reduced phytotoxicity compared to mature, wild-type PAP or PAP-v (Leu20Arg Tyr49His), said PAP mutant containing intact catalytic active site amino acid residues (Glu176, Arg179) and exhibiting anti-viral or anti-fungal activity.

2. The PAP mutant of claim 1, which has altered compartmentalization in vivo compared to wild-type PAP.

3. The PAP mutant of claim 2, having an amino acid substitution at Gly75.

4. The PAP mutant of claim 3, comprising PAP (1-262, Gly75Val).

5. The PAP mutant of claim 1, which includes the N-terminal signal sequence of wild-type PAP.

6. The PAP mutant of claim 1, which includes the C-terminal extension of wild-type PAP.

7. The PAP mutant of claim 2, having an amino acid substitution at Glu97.

8. The PAP mutant of claim 7, which is PAP (1-262, Glu97Lys).

9. The PAP mutant of claim 1, truncated by from at least about 26 to about 76 C-terminal amino acids of mature PAP.

10. The PAP mutant of claim 9, truncated by about 55 C-terminal amino acids of mature PAP.

11. The PAP mutant of claim 10, comprising PAP (1-206Glu).

12. The PAP mutant of claim 9, truncated by about 26 C-terminal amino acids of mature PAP.

13. The PAP mutant of claim 12, comprising PAP (1-236Lys).

14. The PAP mutant of claim 9, truncated by about 76 C-terminal amino acids of mature PAP.

15. The PAP mutant of claim 14, comprising PAP (1-184Glu).

16. The PAP mutant of claim 14, comprising PAP (1-188Lys).

17. The PAP mutant of claim 9, selected from the group consisting of PAP (1-236), PAP (1-235), PAP (1-234), PAP (1-233), PAP (1-232), PAP (1-231), PAP (1-230), PAP (1-229), PAP (1-228), PAP (1-227), PAP (1-226), PAP (1-225), PAP (1-224), PAP (1-223), PAP (1-222), PAP (1-221), PAP (1-220), PAP (1-219), PAP (1-218), PAP (1-217), PAP (1-216), PAP (1-215), PAP (1-214), PAP (1-213), PAP (1-212), PAP (1-211), PAP (1-210), PAP (1-209), PAP (1-208), PAP (1-207), PAP (1-206), PAP (1-205), PAP (1-204), PAP (1-203), PAP (1-202), PAP (1-201), PAP (1-200), PAP (1-199), PAP (1-198), PAP (1-197), PAP (1-196), PAP (1-195), PAP (1-194), PAP (1-193), PAP (1-192), PAP (1-191), PAP (1-190), PAP (1-189), PAP (1-188), PAP (1-187), PAP (1-186), PAP (1-185) and PAP (1-184).

* * * * *

UNITED STATES PATENT AND TRADEMARK OFFICE
CERTIFICATE OF CORRECTION

PATENT NO. : 5,756,322
DATED : May 26, 1998
INVENTOR(S) : Tumer

It is certified that error appears in the above-identified patent and that said Letters Patent is hereby corrected as shown below:

<u>Column 4</u>

Table I, line 45, move "(170)" one place to the right to be underneath "Ala";
Table I, line 48, move "(190)" one place to the left to be underneath "Asn";
Table I, line 57, move "(240)" one place to the left to be underneath "Leu";
Column 6, line 36, change "(1-207" to --(1-207),--;
Column 14, line 37, change "(TTr)" to --(TTT)--;
Column 15, line 6, change "incorporated)" to --(cpm incorporated)--;
Col. 15, ln. 6, the line beginning with "Protein" starts opposite "medium".
Column 17, line 7, change "was" to --were--;
Column 17, line 30, change "pMON8442)" to --(pMON8442)--;
Column 18, line 26, change "T144," to --NT144,--;
Column 19, line 54, change "wks" to --weeks--; and
Column 25, line 40, insert --,-- immediately after "Leu20Arg".

Signed and Sealed this

Twenty-fourth Day of November, 1998

Attest:

Attesting Officer

BRUCE LEHMAN

Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1379 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 225..1163

( i x ) FEATURE:
        ( A ) NAME/KEY: mutation
        ( B ) LOCATION: replace(233, "a")

( i x ) FEATURE:
        ( A ) NAME/KEY: mutation
        ( B ) LOCATION: replace(349, "g")

( i x ) FEATURE:
        ( A ) NAME/KEY: mutation
        ( B ) LOCATION: replace(435, "c")

( x i ) SEQUENCE DESCRIPTION: SEQ ID NO:1:

```
CTATGAAGTC GGGTCAAAGC ATATACAGGC TATGCATTGT TAGAAACATT GATGCCTCTG      60

ATCCCGATAA ACAATACAAA TTAGACAATA AGATGACATA CAAGTACCTA AACTGTGTAT     120

GGGGGAGTGA AACCTCAGCT GCTAAAAAAA CGTTGTAAGA AAAAAAGAAA GTTGTGAGTT     180

AACTACAGGG CGAAAGTATT GGAACTAGCT AGTAGGAAGG GAAG ATG AAG TCG ATG      236
                                                Met Lys Ser Met
                                                 1

CTT GTG GTG ACA ATA TCA ATA TGG CTC ATT CTT GCA CCA ACT TCA ACT      284
Leu Val Val Thr Ile Ser Ile Trp Leu Ile Leu Ala Pro Thr Ser Thr
 5              10                  15                  20

TGG GCT GTG AAT ACA ATC ATC TAC AAT GTT GGA AGT ACC ACC ATT AGC      332
Trp Ala Val Asn Thr Ile Ile Tyr Asn Val Gly Ser Thr Thr Ile Ser
             25                  30                  35

AAA TAC GCC ACT TTT CTG AAT GAT CTT CGT AAT GAA GCG AAA GAT CCA      380
Lys Tyr Ala Thr Phe Leu Asn Asp Leu Arg Asn Glu Ala Lys Asp Pro
         40                  45                  50

AGT TTA AAA TGC TAT GGA ATA CCA ATG CTG CCC AAT ACA AAT ACA AAT      428
Ser Leu Lys Cys Tyr Gly Ile Pro Met Leu Pro Asn Thr Asn Thr Asn
     55                  60                  65

CCA AAG TAC GTG TTG GTT GAG CTC CAA GGT TCA AAT AAA AAA ACC ATC      476
Pro Lys Tyr Val Leu Val Glu Leu Gln Gly Ser Asn Lys Lys Thr Ile
 70                  75                  80

ACA CTA ATG CTG AGA CGA AAC AAT TTG TAT GTG ATG GGT TAT TCT GAT      524
Thr Leu Met Leu Arg Arg Asn Asn Leu Tyr Val Met Gly Tyr Ser Asp
 85                  90                  95                 100

CCC TTT GAA ACC AAT AAA TGT CGT TAC CAT ATC TTT AAT GAT ATC TCA      572
Pro Phe Glu Thr Asn Lys Cys Arg Tyr His Ile Phe Asn Asp Ile Ser
            105                 110                 115

GGT ACT GAA CGC CAA GAT GTA GAG ACT ACT CTT TGC CCA AAT GCC AAT      620
Gly Thr Glu Arg Gln Asp Val Glu Thr Thr Leu Cys Pro Asn Ala Asn
        120                 125                 130

TCT CGT GTT AGT AAA AAC ATA AAC TTT GAT AGT CGA TAT CCA ACA TTG      668
Ser Arg Val Ser Lys Asn Ile Asn Phe Asp Ser Arg Tyr Pro Thr Leu
    135                 140                 145
```

|  |  |  |  |  |  |  |  |  |  |  |  |  |  |  |  |  |
|---|---|---|---|---|---|---|---|---|---|---|---|---|---|---|---|---|
| GAA | TCA | AAA | GCG | GGA | GTA | AAA | TCA | AGA | AGT | CAG | GTC | CAA | CTG | GGA | ATT | 716 |
| Glu | Ser | Lys | Ala | Gly | Val | Lys | Ser | Arg | Ser | Gln | Val | Gln | Leu | Gly | Ile |  |
|  | 150 |  |  |  | 155 |  |  |  |  | 160 |  |  |  |  |  |  |
| CAA | ATA | CTC | GAC | AGT | AAT | ATT | GGA | AAG | ATT | TCT | GGA | GTG | ATG | TCA | TTC | 764 |
| Gln | Ile | Leu | Asp | Ser | Asn | Ile | Gly | Lys | Ile | Ser | Gly | Val | Met | Ser | Phe |  |
| 165 |  |  |  |  | 170 |  |  |  | 175 |  |  |  |  |  | 180 |  |
| ACT | GAG | AAA | ACC | GAA | GCC | GAA | TTC | CTA | TTG | GTA | GCC | ATA | CAA | ATG | GTA | 812 |
| Thr | Glu | Lys | Thr | Glu | Ala | Glu | Phe | Leu | Leu | Val | Ala | Ile | Gln | Met | Val |  |
|  |  |  |  | 185 |  |  |  |  | 190 |  |  |  |  | 195 |  |  |
| TCA | GAG | GCA | GCA | AGA | TTC | AAG | TAC | ATA | GAG | AAT | CAG | GTG | AAA | ACT | AAT | 860 |
| Ser | Glu | Ala | Ala | Arg | Phe | Lys | Tyr | Ile | Glu | Asn | Gln | Val | Lys | Thr | Asn |  |
|  |  |  | 200 |  |  |  |  | 205 |  |  |  |  | 210 |  |  |  |
| TTT | AAC | AGA | GCA | TTC | AAC | CCT | AAT | CCC | AAA | GTA | CTT | AAT | TTG | CAA | GAG | 908 |
| Phe | Asn | Arg | Ala | Phe | Asn | Pro | Asn | Pro | Lys | Val | Leu | Asn | Leu | Gln | Glu |  |
|  |  | 215 |  |  |  |  | 220 |  |  |  |  | 225 |  |  |  |  |
| ACA | TGG | GGT | AAG | ATT | TCA | ACA | GCA | ATT | CAT | GAT | GCC | AAG | AAT | GGA | GTT | 956 |
| Thr | Trp | Gly | Lys | Ile | Ser | Thr | Ala | Ile | His | Asp | Ala | Lys | Asn | Gly | Val |  |
|  | 230 |  |  |  |  | 235 |  |  |  |  | 240 |  |  |  |  |  |
| TTA | CCC | AAA | CCT | CTC | GAG | CTA | GTG | GAT | GCC | AGT | GGT | GCC | AAG | TGG | ATA | 1004 |
| Leu | Pro | Lys | Pro | Leu | Glu | Leu | Val | Asp | Ala | Ser | Gly | Ala | Lys | Trp | Ile |  |
| 245 |  |  |  |  | 250 |  |  |  |  | 255 |  |  |  |  | 260 |  |
| GTG | TTG | AGA | GTG | GAT | GAA | ATC | AAG | CCT | GAT | GTA | GCA | CTC | TTA | AAC | TAC | 1052 |
| Val | Leu | Arg | Val | Asp | Glu | Ile | Lys | Pro | Asp | Val | Ala | Leu | Leu | Asn | Tyr |  |
|  |  |  |  | 265 |  |  |  |  | 270 |  |  |  |  | 275 |  |  |
| GTT | GGT | GGG | AGC | TGT | CAG | ACA | ACT | TAT | AAC | CAA | AAT | GCC | ATG | TTT | CCT | 1100 |
| Val | Gly | Gly | Ser | Cys | Gln | Thr | Thr | Tyr | Asn | Gln | Asn | Ala | Met | Phe | Pro |  |
|  |  |  | 280 |  |  |  |  | 285 |  |  |  |  | 290 |  |  |  |
| CAA | CTT | ATA | ATG | TCT | ACT | TAT | TAT | AAT | TAC | ATG | GTT | AAT | CTT | GGT | GAT | 1148 |
| Gln | Leu | Ile | Met | Ser | Thr | Tyr | Tyr | Asn | Tyr | Met | Val | Asn | Leu | Gly | Asp |  |
|  |  | 295 |  |  |  |  | 300 |  |  |  |  | 305 |  |  |  |  |
| CTA | TTT | GAA | GGA | TTC | TGATCATAAA | CATAATAAGG | AGTATATATA | TATTACTCCA |  |  |  |  |  |  |  | 1203 |
| Leu | Phe | Glu | Gly | Phe |  |  |  |  |  |  |  |  |  |  |  |  |
|  | 310 |  |  |  |  |  |  |  |  |  |  |  |  |  |  |  |

```
ACTATATTAT AAAGCTTAAA TAAGAGGCCG TGTTAATTAG TACTTGTTGC CTTTTGCTTT    1263

ATGGTGTTGT TTATTATGCC TTGTATGCTT GTAATATTAT CTAGAGAACA AGATGTACTG    1323

TGTAATAGTC TTGTTTGAAA TAAAACTTCC AATTATGATG CAAAAAAAAA AAAAAA        1379
```

( 2 ) INFORMATION FOR SEQ ID NO:2:

( i ) SEQUENCE CHARACTERISTICS:
( A ) LENGTH: 313 amino acids
( B ) TYPE: amino acid
( D ) TOPOLOGY: linear ( i i ) MOLECULE TYPE: protein ( x i ) SEQUENCE DESCRIPTION: SEQ ID NO:2:

| Met | Lys | Ser | Met | Leu | Val | Val | Thr | Ile | Ser | Ile | Trp | Leu | Ile | Leu | Ala |
|---|---|---|---|---|---|---|---|---|---|---|---|---|---|---|---|
| 1 |  |  |  | 5 |  |  |  |  | 10 |  |  |  |  | 15 |  |
| Pro | Thr | Ser | Thr | Trp | Ala | Val | Asn | Thr | Ile | Ile | Tyr | Asn | Val | Gly | Ser |
|  |  |  | 20 |  |  |  |  | 25 |  |  |  |  | 30 |  |  |
| Thr | Thr | Ile | Ser | Lys | Tyr | Ala | Thr | Phe | Leu | Asn | Asp | Leu | Arg | Asn | Glu |
|  |  |  | 35 |  |  |  |  | 40 |  |  |  |  | 45 |  |  |
| Ala | Lys | Asp | Pro | Ser | Leu | Lys | Cys | Tyr | Gly | Ile | Pro | Met | Leu | Pro | Asn |
|  | 50 |  |  |  |  | 55 |  |  |  |  | 60 |  |  |  |  |
| Thr | Asn | Thr | Asn | Pro | Lys | Tyr | Val | Leu | Val | Glu | Leu | Gln | Gly | Ser | Asn |
| 65 |  |  |  |  | 70 |  |  |  |  | 75 |  |  |  |  | 80 |
| Lys | Lys | Thr | Ile | Thr | Leu | Met | Leu | Arg | Arg | Asn | Asn | Leu | Tyr | Val | Met |
|  |  |  |  | 85 |  |  |  |  | 90 |  |  |  |  | 95 |  |

```
Gly  Tyr  Ser  Asp  Pro  Phe  Glu  Thr  Asn  Lys  Cys  Arg  Tyr  His  Ile  Phe
               100            105                           110
Asn  Asp  Ile  Ser  Gly  Thr  Glu  Arg  Gln  Asp  Val  Glu  Thr  Thr  Leu  Cys
          115                      120                      125
Pro  Asn  Ala  Asn  Ser  Arg  Val  Ser  Lys  Asn  Ile  Asn  Phe  Asp  Ser  Arg
     130                      135                 140
Tyr  Pro  Thr  Leu  Glu  Ser  Lys  Ala  Gly  Val  Lys  Ser  Arg  Ser  Gln  Val
145                      150                      155                      160
Gln  Leu  Gly  Ile  Gln  Ile  Leu  Asp  Ser  Asn  Ile  Gly  Lys  Ile  Ser  Gly
               165                           170                      175
Val  Met  Ser  Phe  Thr  Glu  Lys  Thr  Glu  Ala  Glu  Phe  Leu  Leu  Val  Ala
               180                      185                      190
Ile  Gln  Met  Val  Ser  Glu  Ala  Ala  Arg  Phe  Lys  Tyr  Ile  Glu  Asn  Gln
          195                      200                      205
Val  Lys  Thr  Asn  Phe  Asn  Arg  Ala  Phe  Asn  Pro  Asn  Pro  Lys  Val  Leu
     210                      215                 220
Asn  Leu  Gln  Glu  Thr  Trp  Gly  Lys  Ile  Ser  Thr  Ala  Ile  His  Asp  Ala
225                      230                 235                           240
Lys  Asn  Gly  Val  Leu  Pro  Lys  Pro  Leu  Glu  Leu  Val  Asp  Ala  Ser  Gly
               245                      250                      255
Ala  Lys  Trp  Ile  Val  Leu  Arg  Val  Asp  Glu  Ile  Lys  Pro  Asp  Val  Ala
          260                      265                      270
Leu  Leu  Asn  Tyr  Val  Gly  Gly  Ser  Cys  Gln  Thr  Thr  Tyr  Asn  Gln  Asn
          275                      280                 285
Ala  Met  Phe  Pro  Gln  Leu  Ile  Met  Ser  Thr  Tyr  Tyr  Asn  Tyr  Met  Val
     290                      295                 300
Asn  Leu  Gly  Asp  Leu  Phe  Glu  Gly  Phe
305                      310
```